United States Patent
Walsdorff et al.

(10) Patent No.: US 7,038,098 B2
(45) Date of Patent: May 2, 2006

(54) METHOD FOR DEHYDROGENATING $C_2$-$C_{30}$-ALKANES

(75) Inventors: Christian Walsdorff, Ludwigshafen (DE); Götz-Peter Schindler, Mannheim (DE); Otto Machhammer, Mannheim (DE); Klaus Harth, Alteiningen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 190 days.

(21) Appl. No.: 10/491,906

(22) PCT Filed: Oct. 14, 2002

(86) PCT No.: PCT/EP02/11467

§ 371 (c)(1),
(2), (4) Date: Apr. 8, 2004

(87) PCT Pub. No.: WO03/033440

PCT Pub. Date: Apr. 24, 2003

(65) Prior Publication Data

US 2004/0199034 A1    Oct. 7, 2004

(30) Foreign Application Priority Data

Oct. 15, 2001  (DE) ................. 101 50 811

(51) Int. Cl.
  *C07C 5/333*  (2006.01)
  *C07C 5/367*  (2006.01)
(52) U.S. Cl. .................. 585/324; 585/319; 585/440; 585/654; 585/659

(58) Field of Classification Search ................ 585/319, 585/324, 440, 654, 659
See application file for complete search history.

(56) References Cited

U.S. PATENT DOCUMENTS

| | | | |
|---|---|---|---|
| 2,376,532 A | 5/1945 | Egloff | |
| 4,788,371 A | 11/1988 | Imai et al. | |
| 5,733,518 A | 3/1998 | Durante et al. | |

FOREIGN PATENT DOCUMENTS

| | | |
|---|---|---|
| EP | 838 534 | 7/2001 |
| WO | 96/33150 | 10/1996 |
| WO | 96/33151 | 10/1996 |
| WO | 01/56960 | 8/2001 |

*Primary Examiner*—Thuan D Dang
(74) *Attorney, Agent, or Firm*—Jason D. Voight

(57) ABSTRACT

$C_2$–$C_{30}$-alkanes are dehydrogenated in a process in which
  (i) ethylbenzene is dehydrogenated to styrene in a first part process to give a hydrogen-containing offgas stream, and
  (ii) one or more $C_2$–$C_{30}$-alkanes are dehydrogenated in the presence of a heterogeneous catalyst in one or more reaction zones in a second part process to give the corresponding olefins, with a hydrogen-containing gas stream being mixed into the reaction gas mixture of the dehydrogenation in at least one reaction zone, wherein at least part of the hydrogen-containing offgas stream obtained in the dehydrogenation of ethylbenzene is mixed into the reaction gas mixture of the alkane dehydrogenation.

8 Claims, No Drawings

METHOD FOR DEHYDROGENATING $C_2$-$C_{30}$-ALKANES

The present invention relates to a process for the heterogeneously catalyzed dehydrogenation of dehydrogenatable $C_2$–$C_{30}$-alkanes.

Dehydrogenated hydrocarbons are required in large quantities as starting materials for numerous industrial processes. For example, dehydrogenated hydrocarbons are used in the production of detergents, high octane gasoline and pharmaceutical products. Likewise, numerous plastics are produced by polymerization of olefins.

For example, acrylonitrile, acrylic acid or $C_4$-oxo alcohols are prepared from propene. Propene is at present prepared predominantly by steam cracking or by catalytic cracking of suitable hydrocarbons or hydrocarbon mixtures such as naphtha.

Propene can also be prepared by heterogeneously catalyzed dehydrogenation of propane.

To achieve acceptable conversions in heterogeneously catalyzed dehydrogenations even in a single pass through the reactor, it is generally necessary to work at relatively high reaction temperatures. Typical reaction temperatures for gas-phase dehydrogenations are from 300 to 700° C. In general, one molecule of hydrogen is produced per molecule of hydrocarbon.

The dehydrogenation of hydrocarbons proceeds endothermically. The heat of dehydrogenation required for achieving a desired degree of conversion has to be introduced either beforehand into the reaction gas and/or during the course of the catalytic dehydrogenation. In most known dehydrogenation processes, the heat of dehydrogenation is generated outside the reactor and is introduced from the outside into the reaction gas. However, this requires complicated reactor and process concepts and leads, particularly, at high conversions, to steep temperature gradients in the reactor, with the risk of increased by-product formation. Thus, for example, a plurality of adiabatic catalyst beds can be installed in a plurality of annular gap reactors connected in series. On its way from one catalyst bed to the next catalyst bed, the reaction gas mixture is superheated by means of heat exchangers and is cooled again in the subsequent pass through a reactor. To achieve high conversions using such a reactor concept, it is necessary either to increase the number of reactors connected in series or to increase the reactor inlet temperature of the gas mixture. The superheating made necessary by this process concept inevitably leads to increased by-product formation as a result of cracking reactions. Another known method is to install the catalyst bed in a tube reactor and to generate the heat of dehydrogenation by burning off combustible gases outside the tube reactor and to introduce the heat into the interior of the reactor via the tube wall. In these reactors, high conversions lead to steep temperature gradients between the wall and the interior of the reaction tube.

An alternative is the generation of the heat of dehydrogenation directly in the reaction gas mixture of the dehydrogenation by oxidation of hydrogen formed in the dehydrogenation or additionally introduced or of hydrocarbons present in the reaction gas mixture by means of oxygen. For this purpose, an oxygen-containing gas and, if appropriate, hydrogen are added to the reaction gas mixture either upstream of the first catalyst bed or upstream of subsequent catalyst beds. At the same time, dispensing with indirect reactor heating achieves a very simple process concept.

U.S. Pat. No. 4,788,371 describes a process for steam dehydrogenation of dehydrogenatable hydrocarbons in the gas phase in combination with oxidative reheating of the intermediates using the same catalyst for the selective oxidation of hydrogen and the steam dehydrogenation. Hydrogen can be introduced as cofeed. The catalyst used comprises a noble metal of group VIII, an alkali metal and a further metal selected from the group consisting of B, Ga, In, Ge, Sn and Pb on an inorganic oxide support such as aluminum oxide. The process can be carried out in one or more stages in a fixed bed or a moving bed.

U.S. Pat. No. 5,733,518 describes a process for the selective oxidation of hydrogen by means of oxygen in the presence of hydrocarbons such as n-butane over a catalyst comprising a phosphate of germanium, tin, lead, arsenic, antimony or bismuth, preferably tin. The heat of reaction necessary for the endothermic dehydrogenation is generated in at least one reaction zone by the combustion of hydrogen.

EP-A 0 838 534 describes a catalyst for the steam-free dehydrogenation of alkanes, in particular isobutane, in the presence of oxygen. The catalyst used comprises a platinum group metal applied to a support comprising tin oxide/zirconium oxide and containing at least 10% of tin. The oxygen content of the feed stream to the dehydrogenation is adjusted so that the quantity of heat produced by combustion of hydrogen with oxygen is equal to the quantity of heat required for the dehydrogenation.

WO 96/33151 describes a process for the dehydrogenation of a $C_2$–$C_5$-alkane in the absence of oxygen over a dehydrogenation catalyst comprising Cr, Mo, Ga, Zn or a group VIII metal with simultaneous oxidation of the hydrogen formed over a reducible metal oxide, e.g. the oxides of Bi, In, Sb, Zn, Tl, Pb or Te. The dehydrogenation has to be interrupted regularly to reoxidize the reduced oxide by means of an oxygen source. U.S. Pat. No. 5,430,209 describes a corresponding process in which the dehydrogenation step and the oxidation step proceed one after the other and the catalysts required for each are physically separate. Catalysts used for the selective oxidation of hydrogen are oxides of Bi, Sb and Te and their mixed oxides.

Finally, WO 96/33150 describes a process in which a $C_2$–$C_5$-alkane is dehydrogenated over a dehydrogenation catalyst in a first stage, the gas leaving the dehydrogenation stage is mixed with oxygen and is, in a second stage, passed over art oxidation catalyst, preferably $Bi_2O_3$, where the hydrogen which has been formed is oxidized selectively to produce water and, in a third stage, the gas leaving the second stage is once again passed over a dehydrogenation catalyst.

The dehydrogenation of ethylbenzene to styrene gives hydrogen as by-product, in a total amount of about 350,000 metric tons per year worldwide. This hydrogen contains secondary constituents, in particular carbon monoxide, carbon dioxide, methane, ethane and ethylene, which frequently do not permit reuse of this hydrogen for hydrogenations since the by-products can poison the hydrogenation catalyst. However, purification of the hydrogen stream to remove the secondary constituents is generally not economical. For these reasons, the hydrogen formed in the dehydrogenation of ethylbenzene is generally burnt, for example for steam generation or superheating of steam.

It is an object of the present invention to provide an advantageous process for the dehydrogenation of alkanes. Another object of the present invention is to find a higher-value use for the hydrogen formed in the dehydrogenation of ethylbenzene.

We have found that these objects are achieved by a process for the heterogeneously catalyzed dehydrogenation of $C_2$–$C_{30}$-alkanes, in which (i) ethylbenzene is dehydrogenated to styrene in a first part process to give a hydrogen-containing offgas stream, and (ii) one or more $C_2$–$C_{30}$-alkanes are dehydrogenated in the presence of a heterogeneous catalyst in one or more reaction zones in a second part process to give the corresponding olefins, with a hydrogen-containing gas stream being mixed into the reaction gas mixture of the dehydrogenation in at least one reaction zone, wherein at least part of the hydrogen-containing offgas stream obtained in the dehydrogenation of ethylbenzene is mixed into the reaction gas mixture of the alkane dehydrogenation.

In the first part process, ethylbenzene is dehydrogenated to styrene. The dehydrogenation of ethylbenzene is generally carried out in the gas phase at from 520 to 650° C. in the presence of a catalyst. It can be carried out at atmospheric pressure, slightly superatmospheric pressure, for example up to about 2 bar, or preferably under a reduced pressure of from about 0.2 to 0.7 bar. Working under reduced pressure shifts the reaction equilibrium to the product side. The dehydrogenation of ethylbenzene is usually carried out in the presence of steam, with the weight ratio of steam: ethylbenzene being from 0.5 to 2.5, preferably from 1.0 to 1.5. The steam added serves as heat transfer medium, stabilizes an intermediate oxidation stage of the catalysts which typically comprise iron oxide and aids the gasification of organic deposits on the catalysts, thus countering carbonization of the catalysts. The organic deposits are converted into carbon monoxide and carbon dioxide. After the reaction gas mixture leaves the dehydrogenation reactor, water and the relatively high-boiling organic components such as styrene, unreacted ethylbenzene and the benzene and toluene formed as by-products are condensed from the reaction gas mixture. This leaves a hydrogen-containing offgas stream which may comprise carbon monoxide and carbon dioxide together with hydrocarbons such as methane, ethane and ethylene and also further constituents.

In general, the offgas stream from the ethylbenzene dehydrogenation contains from 0.1 to 4% by volume of hydrocarbons and from 1.5 to 8% by volume of carbon oxides. The offgas stream from the ethylbenzene dehydrogenation typically comprises from 90 to 97% by volume of hydrogen, from 0.05 to 0.4% by volume of carbon monoxide, from 3 to 7% by volume of carbon dioxide, from 0.1 to 2% by volume of methane, from 0.02 to 0.2% by volume of ethane, from 0.1 to 1.5% by volume of ethylene and a total of from 0 to 2% by volume of water vapor, propane, benzene and/or nitrogen, where the sum of the components specified is 100% by volume.

The hydrogen-containing offgas stream from the dehydrogenation of ethylbenzene is used in the alkane dehydrogenation. It is possible to use either all of the offgas stream or only part thereof. Furthermore, hydrogen from other sources can additionally be used.

The presence of additional hydrogen in the reaction gas mixture of the alkane dehydrogenation counters carbonization of the dehydrogenation catalyst, as a result of which the operating life of the catalyst is increased.

In a preferred embodiment of the process of the present invention, oxygen is additionally mixed into the reaction gas mixture of the alkane dehydrogenation in at least one reaction zone and the added hydrogen present in the reaction gas mixture is burnt, as a result of which at least part of the necessary heat of dehydrogenation is generated directly in the reaction gas mixture in the reaction zone or zones.

Part of the heat of dehydrogenation is generated directly in the reaction gas mixture in at least one reaction zone by exothermic reaction of hydrogen in the presence of oxygen. In general, the total amount of oxygen introduced is, based on the total amount of the alkane to be dehydrogenated, from 0.001 to 0.5 mol/mol, preferably from 0.005 to 0.2 mol/mol, particularly preferably from 0.05 to 0.2 mol/mol. In general, the amount of oxygen added to the reaction gas mixture is chosen so that combustion of the hydrogen present in the reaction gas mixture and any hydrocarbons present in the reaction gas mixture and/or of carbon present in the form of carbon deposits produces the quantity of heat necessary for the dehydrogenation of the alkane to the olefin. In particular embodiments, the heat generated by combustion with oxygen can also be more than or less than the heat required for the dehydrogenation of the hydrocarbon. Oxygen can be used either as pure oxygen or as oxygen-containing gas in admixture with inert gases such as $CO_2$, $N_2$ or the noble gases. A preferred oxygen-containing gas is air. As an alternative to molecular oxygen, it is also possible to use other oxygen-containing gaseous oxidants, for example dinitrogen oxide and ozone. The inert gases and the resulting combustion gases generally have an additional diluting effect and thus promote the heterogeneously catalyzed dehydrogenation.

The hydrogen which is burnt to generate heat is made up of the hydrogen from the ethylbenzene dehydrogenation which is additionally added to the reaction gas mixture and the hydrogen formed in the hydrocarbon dehydrogenation.

In general, hydrogen is added to the reaction gas mixture in such an amount that the molar ratio of $H_2/O_2$ in the reaction mixture directly after the addition is from 0.1 to 200 mol/mol, preferably from 1 to 20 mol/mol, particularly preferably from 2 to 10 mol/mol. In the case of multistage reactors, this applies to each intermediate introduction of hydrogen and oxygen.

The combustion of hydrogen occurs catalytically. The dehydrogenation catalyst used in the second part process generally also catalyzes the combustion of the hydrocarbons and of hydrogen with oxygen, so that in principle no other specific oxidation catalyst is required in principle. In one embodiment of the invention, no specific oxidation catalyst other than the dehydrogenation catalyst is used. In a further embodiment, use is made of one or more oxidation catalysts which selectively catalyze the combustion of hydrogen with oxygen in the presence of hydrocarbons. As a result, the combustion of the hydrocarbons with oxygen to form CO and $CO_2$ proceeds to only a minor extent, which has a significant positive effect on the selectivities achieved for the formation of olefins. The dehydrogenation catalyst and the oxidation catalyst are preferably present in different reaction zones.

In a multistage process, the oxidation catalyst can be present in only one reaction zone, in a plurality of zones or in all reaction zones.

The catalyst which selectively catalyzes the oxidation of hydrogen in the presence of hydrocarbons is preferably located in places at which the prevailing oxygen partial pressures are higher than at other places in the reactor, especially in the vicinity of the feed point for the oxygen-containing gas. The oxygen-containing gas and/or hydrogen can be fed in at one or more points in the reactor.

A preferred catalyst, which selectively catalyzes the combustion of hydrogen, comprises oxides or phosphates selected from the group consisting of the oxides and phosphates of germanium, tin, lead, arsenic, antimony and bismuth.

A further preferred catalyst which catalyzes the combustion of hydrogen comprises a noble metal of transition group VIII and/or I.

Dilution of the reaction gas mixture with inert gas, increasing the reaction temperature and/or reducing the reaction pressure allow the thermodynamically possible limiting conversions to be increased to above the desired reaction conversions. In this way, for example, space-time yields of above 1 kg of propene/kg of catalyst*h can be achieved in the dehydrogenation of propane. The space velocity (GSHV) over the catalyst can be >4000 $h^{-1}$ in this mode of operation, also known as high load operation.

The dehydrogenation catalyst can be regenerated in a manner known per se. Thus, as described above, steam can be added to the reaction gas mixture. Carbon which is deposited under these reaction conditions can be partially or completely removed by the principle of coal gasification.

As an alternative, an oxygen-containing gas can from time to time be passed over the catalyst bed at elevated temperature and the carbon deposits can be burned off in this way.

After a prolonged period of operation, the dehydrogenation catalyst is preferably regenerated by firstly flushing it with inert gas at from 300 to 600° C., frequently from 350 to 500° C., and subsequently, in a first regeneration step, passing air diluted with nitrogen or steam over the catalyst bed. The space velocity over the catalyst is preferably from 50 to 10,000 $h^{-1}$ and the oxygen content is from about 0.5 to 2% by volume. In further, subsequent regeneration steps, the oxygen content is gradually increased to about 20% by volume (pure air). Preference is given to carrying out from 2 to 10, particularly preferably from 2 to 5, regeneration steps. In general, this is followed by regeneration using pure hydrogen or hydrogen diluted with an inert gas (hydrogen content >1% by volume) under otherwise identical conditions. All regeneration steps are preferably carried out in the presence of steam.

The alkane dehydrogenation in the second part process of the process of the present invention can in principle be carried out in all types of reactor and by all methods known from the prior art. The additional introduction of hydrogen and oxygen leads to at least part of the heat of reaction or the energy required for heating the reaction gas mixture being generated by direct combustion and not having to be introduced indirectly via heat exchangers.

A comprehensive description of suitable types of reactor and methods of operation may also be found in "Catalytica® Studies Division, Oxidative Dehydrogenation and Alternative Dehydrogenation Processes, Study Number 4192 OD, 1993, 430 Ferguson Drive, Mountain View, Calif., 94043-5272 USA"

A suitable type of reactor is a fixed-bed tube reactor or a shell-and-tube reactor. In these, the catalyst (dehydrogenation catalyst and, if appropriate, specific oxidation catalyst) is located as a fixed bed in a reaction tube or in a bundle of reaction tubes. The reaction tubes are customarily heated indirectly by a gas, e.g. a hydrocarbon such as methane, being burnt in the space surrounding the reaction tubes. It is advantageous to apply this indirect form of heating to only the first about 20–30% of the length of the fixed bed and to heat the remainder of the bed to the necessary reaction temperature by means of the radiant heat given off from the indirect heating. The indirect heating of the reaction gas can, according to the present invention, advantageously be combined with direct heating by combustion in the reaction gas mixture. Combining the direct introduction of heat with indirect introduction of heat makes it possible to achieve approximately isothermal reaction conditions. Customary internal diameters of the reaction tubes are from about 10 to 15 cm. A typical shell-and-tube reactor used for dehydrogenation comprises from about 300 to 1000 reaction tubes. The temperature in the interior of the reaction tubes is usually in the range from 300 to 700° C., preferably in the range from 400 to 700° C. The operating pressure is usually from 0.5 to 8 bar, frequently from 1 to 2 bar when using low steam dilution (corresponding to the BASF-Linde process) but also from 3 to 8 bar when using high steam dilution (corresponding to the steam active reforming process (STAR process) of Phillips Petroleum Co., cf. U.S. Pat. No. 4,902,849, U.S. Pat. No. 4,996,387 and U.S. Pat. No. 5,389,342). In general, the product mixture leaves the reaction tube at a temperature which has been decreased by 50–100° C. Typical space velocities of propane over the catalyst are from 500 to 2000 $h^{-1}$. The catalyst geometry can be, for example, spherical or cylindrical (hollow or solid).

The alkane dehydrogenation in the second part process of the process of the present invention can be carried out in a moving-bed reactor. For example, the moving catalyst bed can be accommodated in a radial flow reactor. In this, the catalyst slowly moves from the top downward, while the reaction gas mixture flows radially. This method is, for example, employed in the UOP-Oleflex dehydrogenation process. Since the reactors in this process are operated pseudoadiabatically, it is advantageous to employ a plurality of reactors connected in series (typically up to four reactors). Upstream of or in each reactor, the gas mixture entering the reactor is heated to the necessary reaction temperature by combustion in the presence of the oxygen introduced. The use of a plurality of reactors allows large differences in the temperature of the reaction gas mixture between reactor inlet and reactor outlet to be avoided and nevertheless allows high overall conversions to be achieved.

When the catalyst bed has left the moving-bed reactor, it is passed to regeneration and subsequently reused. The dehydrogenation catalyst used generally has a spherical shape. The operating pressure is typically from 2 to 5 bar. The molar ratio of hydrogen to propane is preferably from 0.1 to 10. The reaction temperatures are preferably from 550 to 660° C.

An alkane dehydrogenation in the second part process of the process of the present invention can also be carried out, as described in Chem. Eng. Sci. 1992 b, 47 (9–11) 2313, in a fluidized bed of heterogeneous catalyst, with the hydrocarbon not being diluted. It is advantageous to employ two fluidized beds of which one is generally being regenerated. The operating pressure is typically from 1 to 2 bar, and the dehydrogenation temperature is generally from 550 to 600° C. The heat required for the dehydrogenation is introduced into the reaction system by preheating the dehydrogenation catalyst to the reaction temperature. Mixing in a hydrogen-containing cofeed and an oxygen-containing cofeed enables the preheater to be dispensed with and the heat required to be generated directly in the reactor system by combustion of hydrogen in the presence of oxygen.

In a particularly preferred embodiment of the process of the present invention, the alkane dehydrogenation in the second part process is carried out in a tray reactor. This contains one or more successive catalyst beds. The number of catalyst beds can be from 1 to 20, advantageously from 2 to 8, in particular from 4 to 6. The reaction gas preferably flows radially or axially through the catalyst beds. In general, such a tray reactor is operated using a fixed catalyst bed.

In the simplest case, the fixed catalyst beds are located axially or in the annular gaps of concentric cylindrical gratings in a shaft furnace reactor. One shaft furnace reactor corresponds to one tray. It is possible to carry out the dehydrogenation in a single shaft furnace reactor, but this is less preferred.

In one operating mode without oxygen as cofeed, the reaction gas mixture is subjected to intermediate heating on its way from one catalyst bed to the next catalyst bed in the tray reactor, e.g. by passing it over heat exchange ribs heated with hot gases or by passing it through tubes heated with hot combustion gases.

In the preferred variant of the process of the present invention, intermediate heating of the reaction gas mixture is carried out at least partly by direct means. For this purpose, hydrogen-containing offgas from the ethylbenzene dehydrogenation and molecular oxygen are added in limited amounts to the reaction gas mixture either before it flows through the first catalyst bed and/or between the subsequent catalyst beds. In this way, hydrogen added in limited amounts and also hydrogen formed during the dehydrogenation, hydrocarbons present in the reaction gas mixture and/or carbon or carbon-like compounds which have been deposited on the catalyst surface are burnt over the catalyst. The heat of reaction liberated in this way thus allows virtually isothermal operation of the heterogeneously catalyzed hydrocarbon dehydrogenation.

In one embodiment of the process of the present invention, intermediate introduction of oxygen-containing gas and hydrogen-containing dehydrogenation offgas is carried out upstream of each tray of the tray reactor. In a preferred embodiment, a bed of a specific oxidation catalyst is present downstream of each introduction point, followed by a bed of the dehydrogenation catalyst. In a second preferred embodiment, no specific oxidation catalyst is present.

The dehydrogenation temperature is generally from 400 to 800° C., and the pressure is generally from 0.2 to 5 bar, preferably from 0.5 to 2 bar, particularly preferably from 1 to 1.5 bar. The space velocity (GSHV) is generally from 500 to 2000 $h^{-1}$, in high-load operation also up to 16,000 $h^{-1}$, preferably from 4000 to 16,000 $h^{-1}$.

The dehydrogenation catalysts used in the second part process of the process of the present invention generally comprise a support and an active composition. The support is composed of a heat-resistant oxide or mixed oxide. The dehydrogenation catalysts preferably comprise a metal oxide selected from the group consisting of zirconium dioxide, zinc oxide, aluminum oxide, silicon dioxide, titanium dioxide, magnesium oxide, lanthanum oxide, cerium oxide and mixtures thereof as support. Preferred supports are zirconium dioxide and/or silicon dioxide, particularly preferably mixtures of zirconium dioxide and silicon dioxide.

The active compositions of the dehydrogenation catalysts generally comprise one or more elements of transition group VIII, preferably platinum and/or palladium, particularly preferably platinum. The dehydrogenation catalysts can further comprise one or more elements of main groups I and/or II, preferably potassium and/or cesium. Furthermore, the dehydrogenation catalysts may further comprise one or more elements of transition group III including the lanthanides and actinides, preferably lanthanum and/or cerium. Finally, the dehydrogenation catalysts may further comprise one or more elements of main groups III and/or IV, preferably one or more elements selected from the group consisting of boron, gallium, silicon, germanium, tin and lead, particularly preferably tin.

In a preferred embodiment, the dehydrogenation catalyst comprises at least one element of transition group VIII, at least one element of main groups I and/or II, at least one element of main groups III and/or IV and at least one element of transition group III including the lanthanides and actinides.

To produce the dehydrogenation catalysts, it is possible to use precursors for oxides of zirconium, silicon, aluminum, titanium, magnesium, lanthanum or cerium which can be converted into the oxides by calcination. These can be prepared by known methods, for example by the sol-gel process, precipitation of the salts, dehydration of the corresponding acids, dry mixing, slurrying or spray drying. For example, a $ZrO_2.Al_2O_3.SiO_2$ mixed oxide can be prepared by firstly preparing a water-rich zirconium oxide of the formula $ZrO_2.xH_2O$ by precipitation of a suitable zirconium-containing precursor. Suitable zirconium-containing precursors are, for example, $Zr(NO_3)_4$, $ZrOCl_2$ or $ZrCl_4$. The precipitation itself is achieved by addition of a base such as NaOH, KOH, $Na_2CO_3$ and $NH_3$ and is described, for example, in EP-A 0 849 224.

To prepare a $ZrO_2.SiO_2$ mixed oxide, the previously obtained zirconium-containing precursor can be mixed with a silicon-containing precursor. Suitable precursors for $SiO_2$ are, for example, water-containing sols of $SiO_2$ such as Ludox™. Mixing of the two components can be carried out, for example, by simple mechanical mixing or by spray drying in a spray dryer.

To prepare a $ZrO_2.SiO_2.AL_2O_3$ mixed oxide, the $SiO_2.ZrO_2$ powder mixture obtained as described above can be admixed with an aluminum-containing precursor. This can be carried out, for example, by simple mechanical mixing in a kneader. However, the preparation of $ZrO_2.SiO_2.AL_2O_3$ mixed oxide can also be carried out in a single step by dry mixing the individual precursors.

The supports for the dehydrogenation catalysts have the advantage, inter alia, that they can readily be shaped. For this purpose, the powder mixture obtained is admixed with a concentrated acid in the kneader and then converted into a shaped body, e.g. by means of a ram extruder or a screw extruder.

In particular embodiments, the dehydrogenation catalysts have a defined pore structure. When using mixed oxides, it is possible for the pore structure to be influenced in a targeted manner. The particle sizes of the various precursors influence the pore structure. Thus, for example, macropores can be generated in the microstructure by use of $Al_2O_3$ having a low loss on ignition and a defined particle size distribution. The use of $Al_2O_3$ having a loss on ignition of about 3% (e.g. Puralox®) has been found to be advantageous for this purpose.

A further possible way of producing supports having a specific pore radius distribution for the dehydrogenation catalysts used according to the present invention is to add, during production of the support, various polymers which can be partly or completely removed by calcination so as to form pores in defined pore radius ranges. Mixing of the polymers and the oxide precursors can be carried out, for example, by simple mechanical mixing or by spray drying in a spray dryer.

The use of PVP (polyvinylpyrrolidone) has been found to be particularly advantageous for producing supports having a bimodal pore radius distribution. If this is added to one or more oxide precursors for oxides of the elements Zr, Ti, Al or Si in a production step, macropores in the range from 200 to 5000 nm are formed after calcination. A further advantage of the use of PVP is the easier shapability of the support.

Thus, extrudates having good mechanical properties can easily be produced from freshly precipitated water-containing $ZrO_2 \cdot x\ H_2O$ which has previously been dried at 120° C. when PVP and formic acid are added, even without further oxide precursors.

Calcination of the supports for the dehydrogenation catalysts is advantageously carried out after application of the active components and is carried out at from 400 to 1000° C., preferably from 500 to 700° C., particularly preferably from 550 to 650° C. and in particular from 560 to 620° C. The calcination temperature should usually be at least as high as the reaction temperature of the dehydrogenation in which these dehydrogenation catalysts are to be used.

After calcination, the supports of the dehydrogenation catalysts generally have high BET surface areas. The BET surface areas are generally greater than 40 $m^2/g$, preferably greater than 50 $m^2/g$, particularly preferably greater than 70 $m^2/g$. The pore volume of the dehydrogenation catalysts used according to the present invention is usually from 0.2 to 0.6 ml/g, preferably from 0.25 to 0.5 ml/g. The mean pore diameters of the dehydrogenation catalysts used according to the present invention, which can be determined by Hg porosimetry, is in the range from 3 to 20 nm, preferably from 4 to 15 nm.

The dehydrogenation catalysts used preferably have a bimodal pore radius distribution. The pore radii are in the ranges up to 20 nm and from 40 to 5000 nm. Based on the total pore volume of the dehydrogenation catalyst, the total proportion of these pores is at least 70%. The proportion of pores having pore radii below 20 nm is generally from 20 to 60%, and the proportion of pores having pore radii of from 40 to 5000 nm is generally likewise from 20 to 60%.

The application of the dehydrogenation-active component, usually a metal of transition group VIII, is generally carried out by impregnation with a suitable metal salt precursor. However, in place of impregnation, the dehydrogenation-active component can also be applied by other methods, for example spray-on of the metal salt precursor. Suitable metal salt precursors are, for example, the nitrates, acetates and chlorides of the appropriate metals; complex anions of the metals to be used are also possible. Preference is given to using platinum as $H_2PtCl_6$ or $Pt(NO_3)_2$. Suitable solvents for the metal salt precursors are water and organic solvents. Particularly useful solvents are water and lower alcohols such as methanol and ethanol.

When using noble metals as dehydrogenation-active components, suitable precursors also include the corresponding noble metal sots which can be prepared by one of the known methods, for example by reduction of a metal salt with a reducing agent in the presence of a stabilizer such as PVP. The technique is described in detail in the German patent application DE 195 00 366.

The amount of noble metal present as dehydrogenation-active component in the dehydrogenation catalysts is from 0 to 5% by weight, preferably from 0.05 to 1% by weight, particularly preferably from 0.05 to 0.5% by weight.

The further components of the active composition can be applied either during preparation of the support, for example by coprecipitation, or subsequently, for example by impregnation of the support with suitable precursor compounds. Precursor compounds used are generally compounds which can be converted into the corresponding oxides by calcination. Suitable precursors are, for example, hydroxides, carbonates, oxalates, acetates, chlorides or mixed hydroxycarbonates of the appropriate metals.

In advantageous embodiments, the active composition further comprises the following additional components:

at least one element from main group I or II, preferably cesium and/or potassium, in an amount of from 0 to 20% by weight, preferably from 0.1 to 15% by weight, particularly preferably from 0.2 to 10% by weight;

at least one element of transition group III including the lanthanides and actinides, preferably lanthanum and/or cerium, in an amount of from 0 to 20% by weight, preferably from 0.1 to 15% by weight, particularly preferably from 0.2 to 10% by weight;

at least one element of main groups III and IV, preferably tin, in an amount of from 0 to 10% by weight.

The dehydrogenation catalyst is preferably halogen-free.

The dehydrogenation catalyst can be present in the reactor as a fixed bed or can be used, for example, in the form of a fluidized bed, and can have a corresponding shape. Examples of suitable shapes are granules, pellets, monoliths, spheres or extrudates (rods, wagon wheels, stars, rings).

Dehydrogenatable alkanes used are straight-chain or branched alkanes having from 2 to 30 carbon atoms. The process is particularly useful for the dehydrogenation of straight-chain or branched alkanes having a chain length of from 2 to 15 carbon atoms, preferably from 2 to 5 carbon atoms. Examples are ethane, propane, n-butane, isobutane, n-pentane, isopentane, n-hexane, n-heptane, n-octane, n-nonane, n-decane, n-undecane, n-dodecane, n-tridecane, n-tetradecane, n-pentadecane and mixtures thereof. A particularly preferred alkane is propane.

Since the dehydrogenation reaction is accompanied by an increase in volume, the conversion can be increased by lowering the partial pressure of the reactants. This can be achieved, for example, in a simple manner by carrying out the dehydrogenation under reduced pressure and/or by addition of an inert gas. Suitable inert gases are, for example, nitrogen, steam, carbon dioxide and noble gases such as He, Ne or Ar. Preference is given to diluents which are inert under the reaction conditions (i.e. change chemically to an extent of less than 5 mol %, preferably less than 3 mol % and more preferably less than 1 mol %). Dilution with steam is generally accompanied by the further advantage of reduced carbonization of the dehydrogenation catalyst used according to the present invention and thus an increased operating life, since the steam reacts with carbon deposits according to the principle of coal gasification. The ratio of steam to the hydrocarbon to be dehydrogenated is in the range from 0 to 10 mol/mol, preferably from 0.1 to 5 mol/mol.

The alkane used in the second part process of the process of the present invention does not have to be a pure compound. Rather, the alkane can further comprise gases such as methane, ethylene, propene, butenes, propyne, acetylene or $H_2S$. In particular, the dehydrogenation of the present invention can also be carried out using alkane mixtures such as LPG (liquefied petroleum gas) which are produced industrially and are available in large amounts.

The output from the reactor is worked up in a manner known per se, for example by separating off the molecular hydrogen present in the product mixture, separating off the constituents other than alkanes and alkenes, preferably by selective absorption of the alkene/alkane mixture in an organic solvent, and fractionating the alkene/alkane mixture in a $C_3$ splitter and recirculating the alkane to the dehydrogenation.

In the case of propane as alkane to be dehydrogenated, the process of the present invention can be carried out as the first stage of a process for preparing acrolein and/or acrylic acid from propane. In this case, propane is subjected to an autothermal dehydrogenation to give a gas mixture comprising propane and propene, propane and propene are separated off from the product gas mixture from the dehydrogenation and this propane/propene mixture is passed to an oxidation reactor in which propene is subjected to a selective, heterogeneously catalyzed gas-phase oxidation by means of oxygen to form acrolein and/or acrylic acid. Acrolein/acrylic acid is/are separated off from the product gas mixture from the oxidation and the remaining gas mixture, which comprises, inter alia, unreacted propane, is recirculated to the alkane dehydrogenation. Analogously, the process of the present invention using ethane as alkane to be dehydrogenated can be employed as first stage of a process for preparing ethylbenzene from ethane and benzene, the process using propane as alkane to be dehydrogenated can be employed as first stage of a process for preparing cumene from propane and benzene and the process using higher alkanes can be employed as first stage of a process for preparing linear alkylbenzenes from the higher alkanes and benzene. The gas mixture which remains after the product has been separated off and comprises, inter alia, unreacted alkane can in each case be recirculated to the alkane dehydrogenation.

We claim:

1. A process for the dehydrogenation of $C_2$–$C_{30}$-alkanes, in which
   (i) ethylbenzene is dehydrogenated to styrene in a first part process to give a hydrogen-containing offgas stream, and
   (ii) one or more $C_2$–$C_{30}$-alkanes are dehydrogenated in the presence of a heterogeneous catalyst in one or more reaction zones in a second part process to give the corresponding olefins, with a hydrogen-containing gas stream being mixed into the reaction gas mixture of the alkane dehydrogenation in at least one reaction zone, and wherein oxygen is additionally mixed into the reaction gas mixture of the alkane dehydrogenation in at least one reaction zone and the hydrogen present in the reaction gas mixture is thereby burnt, as a result of which at least part of the necessary heat of dehydrogenation is generated directly in the reaction gas mixture in the reaction zone or zones, wherein at least part of the hydrogenation-containing offgas stream obtained in the dehydrogenation of ethylbenzene is mixed into the reaction gas mixture of the alkane dehydrogenation.

2. A process as claimed in claim 1, wherein the offgas stream from the ethylbenzene dehydrogenaton which is mixed into the reaction gas mixture of the alkane dehydrogenation contains from 0.1 to 4% by volume of hydrocarbons and from 1.5 to 8% by volume of carbon oxides.

3. A process as claimed in claim 1, wherein the offgas stream from the ethylbenzene dehydrogenation which is mixed into the reaction gas mixture of the alkane dehydrogenation comprises from 90 to 97% by volume of hydrogen, from 0.05 to 0.4% by volume of carbon monoxide, from 3 to 7% by volume of carbon dioxide, from 0.1 to 2% by volume of methane, from 0.02 to 0.2% by volume of ethane, from 0.1 to 1.5% by volume of ethylene and a total of from 0 to 2% by volume of water vapor, propane, benzene and/or nitrogen, where the sum of the components specified is 100% by volume.

4. A process as claimed in claim 1, wherein the alkane dehydrogenation catalyst comprises at least one metal oxide selected from the group consisting of zirconium dioxide, aluminum oxide, silicon dioxide, titanium dioxide, magnesium oxide, lanthanum oxide and cerium oxide, at least one element of transition group VIII, at least one element of main group I or II, at least one element of main group III or IV and at least one element of transition group III including the lanthanides and actinides.

5. A process as claimed in claim 4, wherein the alkane dehydrogenation catalyst comprises zirconium dioxide and/or silicon dioxide, platinum and/or palladium, cesium and/or potassium, lanthanum and/or cerium and tin.

6. A process as claimed in claim 1, wherein at least one reaction zone of the alkane dehydrogenation contains a catalyst which selectively catalyzes the combustion of hydrogen with oxygen in the presence of hydrocarbons.

7. A process as claimed in claim 1, wherein steam is mixed into the reaction gas mixture of the alkane dehydrogenation.

8. A process as claimed in claim 1, wherein the alkane dehydrogenation is carried out in a tray reactor having from 2 to 8 catalyst beds.

* * * * *